United States Patent [19]

Coffindaffer et al.

[11] Patent Number: 5,624,666
[45] Date of Patent: Apr. 29, 1997

[54] ANTI-DANDRUFF SHAMPOOS WITH PARTICULATE ACTIVE AGENT AND CATIONIC POLYMER

[75] Inventors: Timothy W. Coffindaffer; Philip E. Cothran, both of Loveland; Thomas F. Gauthier, Milford, all of Ohio

[73] Assignee: The Procter & Gamble Company, Cincinnati, Ohio

[21] Appl. No.: 375,457

[22] Filed: Jan. 20, 1995

[51] Int. Cl.$^6$ ................................................ A61K 7/06
[52] U.S. Cl. .......................... 424/70.21; 424/70.22; 424/70.24; 424/70.28; 514/880; 514/881
[58] Field of Search ....................... 424/70.21, 70.22, 424/70.24, 70.28; 514/880, 881

[56] References Cited

U.S. PATENT DOCUMENTS

| | | | |
|---|---|---|---|
| 4,273,760 | 6/1981 | Koehler et al. | 424/70.24 |
| 4,298,494 | 11/1981 | Parslow et al. | 252/550 |
| 4,830,774 | 5/1989 | LaPetina et al. | 514/852 |
| 4,835,148 | 5/1989 | Barford et al. | 514/881 |
| 4,997,641 | 3/1991 | Hartnett et al. | 424/70.28 |
| 5,104,645 | 4/1992 | Cardin et al. | 514/852 |
| 5,145,607 | 9/1992 | Rich | 424/70.28 |
| 5,149,522 | 9/1992 | Schwarz et al. | 424/70.28 |
| 5,393,519 | 2/1995 | Dowell et al. | 424/70.24 |

*Primary Examiner*—Mark D. Sweet
*Attorney, Agent, or Firm*—Leonard W. Lewis; Anthony D. Sabatelli; David K. Dabbiere

[57] ABSTRACT

Provided is a anti-dandruff shampoo composition comprising: (a) from about 8% to about 40%, by weight, of anionic detersive surfactant; (b) from about 0.1% to about 5%, by weight, of particulate anti-dandruff agent having an average particle size of from about 0.35 microns to about 5 microns; (c) from about 0.01% to about 1.0%, by weight, of a stabilizing agent for said anti-dandruff agent, said stabilizing agent being a soluble cationic polymer; (d) from about 50% to about 91.89%, by weight, water; wherein said shampoo composition is substantially free of suspending agents selected from the group consisting of crystalline suspending agents and anionic, nonionic, and amphoteric polymeric suspending agents. Also provided is a process used for making the present compositions wherein said particulate anti-dandruff agent and said cationic polymer are admixed in water in the presence of anionic detersive surfactant.

17 Claims, No Drawings

ANTI-DANDRUFF SHAMPOOS WITH PARTICULATE ACTIVE AGENT AND CATIONIC POLYMER

TECHNICAL FIELD

The present invention relates to shampoo compositions containing particulate anti-dandruff agents. In particular, the present invention relates to shampoo compositions containing a particulate anti-dandruff agent and a cationic polymer.

BACKGROUND OF THE INVENTION

Shampoo compositions for cleaning the hair which also contain anti-dandruff agents are well known. Among the preferred types of anti-dandruff agents are particulate, crystalline anti-dandruff agents, such as sulfur, selenium disulfide, and heavy metal salts of pyridinethione. In order for these types of shampoos to be effective and to provide a consistent level of performance, without requiring vigorous shaking of the package in which they are contained, it is conventional practice to suspend them in the composition with the aid of a suspending agent. Since shampoos are likely to remain on shelves or in storage for long periods of time, it is important for the suspending agents to keep the particulate anti-dandruff agents well suspended for relatively long periods of time. The suspending agents which have become preferred for suspension of particulate anti-dandruff agents are those which form a crystalline network in the shampoo when the shampoo is stationary, but which allow the composition to readily flow when shear is applied, such as when a user pours it out of a bottle. Examples of such suspending agents include ethylene glycol distearate and N, N- di- (hydrogenated tallow) amido benzoic acid. Crystalline suspending agents are currently the preferred method for suspending particulate anti-dandruff agents in the marketplace.

Other suspending agents which are known include hydrophilic polymeric thickening agents such as cellulosic gums and acrylic acid/acrylate polymers, the latter of which are commonly referred to as carbomers. Although these materials are effective for suspending particulate matter, at higher levels they tend to impart an undesirable, slimy feel.

Just as important as suspending the anti-dandruff agent, the suspending agent must also allow the anti-dandruff agent to deposit on the scalp during use. If too little anti-dandruff agent deposits, it will be unable to provide good anti-dandruff efficacy. The polymeric suspending agents are believed to be less efficient than the crystalline suspending agents for deposition of active ingredients on the scalp and hair.

Another drawback of crystalline suspending agent is that they require costly heating and cooling steps in the manufacture of the compositions in order to make high quality stable suspensions.

Another important parameter in the formulation of anti-dandruff shampoos is lathering. The consuming public often associates high lathering with effective cleaning, and typically prefers high lathering shampoos to low lathering shampoos from an aesthetic standpoint. Unfortunately, crystalline suspending agents tend to adversely affect lathering performance.

It is also known to prepare antimicrobial compositions utilizing finely powdered polyvalent metal salts of 2-mercaptopyridine-N-oxide, e.g., zinc pyridinethione. See, for example, U.S. Pat. No. 4,832,950 (Takaya et al., issued May 23, 1989) and U.S. Pat. No. 4,670,430 (Inamura et al., issued Jun. 2, 1987). In these compositions, very small average particle size of less than 0.2 microns, are said to provide improved dispersion stability without the use of polymeric suspending agents or other means to suspend larger particles. Compared to such prior compositions, the compositions of Imamura et al. are said to provide improved adsorbability. Takaya et al. teaches further suspension stability of the small particles of Imamura et al. via the use of a specific dispersent selected from the group consisting of: (A) polyglycol/polyamine polyglycol/polyamine/ alkylamine or alkyleneamine condensation polymers; (B) water soluble polymers selected from the group consisting of hydroxyalkylcelluloses and partly quaternized products thereof, and at least one nonionic surfactant; and (C) at least one cationic polymer compound and at least one inorganic salt.

Although the above compositions avoid the use of conventional suspending agents, deposition efficiency of the particulate metal salts remains impaired due to the extremely small size of these particles. Because of their small size, a proportion of them would tend to remain dispersed in solution rather than deposit on the scalp, skin, or hair.

Thus, it would be desirable to provide liquid topical composition with a stable dispersed anti-dandruff agent, which utilized larger particles than those specified in the above patents, but which also did not require the use of conventional suspending agents such as crystalline suspending agents or polymers added for thickening purposes.

It is an object of this invention to provide anti-dandruff shampoos containing particulate anti-dandruff agents that are suspended without the need for crystalline suspending agents, but which still retain efficient deposition of the anti-dandruff agent on the hair or scalp. It is another object of this invention to provide anti-dandruff shampoos containing particulate anti-dandruff agents that are suspended without the need for hydrophilic polymeric thickening agents, but which still retain efficient deposition of the anti-dandruff agent on the hair or scalp.

It is another object of this invention to provide such compositions, as set forth above, which have good, non-slimy feel. It is yet another object of this invention to provide compositions as set forth above which have improved deposition efficiency on the skin, scalp and/or hair, relative to conventional suspending agents for particulate matter in liquid topical compositions. It is still another object of this invention to provide compositions, as set forth above, which can be made without the need for costly heating and cooling steps, as conventionally utilized when crystalline suspending agents are employed.

It is yet another object of this invention to provide a process for making anti-dandruff shampoos meeting the above objects.

These and other benefits as may be apparent or otherwise realized can be obtained according to the present invention, which is described below.

Unless otherwise indicated, all percentages are calculated by weight of the total composition, and all ratios are calculated on a weight basis. Unless otherwise indicated, ingredients are based on the active level and, therefore do not include carriers or by-products that may be included in commercially available materials. The present invention may comprise, consist of, or consist essentially of any of the essential and various optional and/or preferred ingredients and elements described herein.

SUMMARY OF THE INVENTION

It has now been found that anti-dandruff shampoos meeting the above objects can be achieved. In particular, it has been found that relatively small particle size particulate anti-dandruff agents can be suspended in shampoo compositions containing anionic surfactants and relatively low levels of a shampoo soluble cationic polymer, without the need for crystalline suspending agents or polymeric thickening agents for suspending the particles. The present compositions utilize particles having an average particle diameter of from about 0.35 microns to about 5 microns. By way of theory, and without intending to necessarily limit the invention, it is believed that the cationic polymers hereof form a net-like suspension by bridging miscelles of the anionic surfactant. The small particle size particulate anti-dandruff agent then becomes suspended within this network.

More specifically, the present invention provides an anti-dandruff shampoo composition comprising:

(a) from about 8% to about 40%, by weight, of anionic detersive surfactant;

(b) from about 0.1% to about 5%, by weight, of particulate anti-dandruff agent having an average particle size of from about 0.35 microns to about 5 microns;

(c) from about 0.01% to about 1.0%, by weight, of a stabilizing agent for said anti-dandruff agent, said stabilizing agent being a soluble cationic polymer;

(d) from about 50% to about 91.89%, by weight, water; wherein said shampoo composition is substantially free of suspending agents selected from the group consisting of crystalline suspending agents and anionic, nonionic, and amphoteric polymeric suspending agents.

It has also been found that the process used for making the present compositions can be critical to stability of the final product. In particular, the particulate anti-dandruff agent and cationic polymer should preferably be combined or admixed with one another only in aqueous conditions in the presence of anionic surfactant. Combining the particulate anti-dandruff agent and cationic polymer under aqueous conditions, in the absence of anionic surfactant can undesireably lead to agglomeration of the particulate anti-dandruff agent.

More specifically, the present invention provides a process for making a stable anti-dandruff shampoo composition comprising preparing a mixture of:

(a) from about 8% to about 40%, by weight, anionic detersive surfactant;

(b) from about 0.1% to about 5%, by weight, of particulate anti-dandruff agent having a volume average particle size of from about 0.35 microns to about 5 microns;

(c) from about 0.01% to about 1%, by weight, of stabilizing agent for said anti-dandruff agent, said stabilizing agent being a shampoo soluble cationic polymer;

(d) from about 50% to about 91.89%, by weight, water; wherein said particulate anti-dandruff agent and said cationic polymer are admixed in water in the presence of anionic detersive surfactant, and said composition is substantially free of crystalline suspending agents and anionic, amphoteric, and nonionic polymeric suspending agents.

The present invention can provide shampoos with excellent anti-dandruff efficacy, cleansing, and lathering. In addition, the present invention can result in significant cost savings in view of the elimination of conventional suspending agents, which are typically used at higher levels than are the cationic polymers of the present invention, or which in the case of crystalline suspending agents require separate heating and cooling steps to process the suspending material. In addition, the compositions hereof can provide enhanced lathering and excellent deposition of anti-dandruff actives on the skin, scalp and/or hair.

DETAILED DESCRIPTION OF THE INVENTION

Detersive Surfactant Component

The compositions of the present invention contain an anionic detersive surfactant component, which preferably comprises alkyl sulfate, alkyl ethoxylated sulfate, or a mixture thereof. The compositions hereof can also comprise other types of anionic surfactants, and can additionally contain nonionic and amphoteric surfactants.

The anionic detersive surfactant component will generally be present at a level from about 8% to about 40%, by weight of the composition, preferably from about 10% to about 30%, more preferably from about 12% to about 22%.

Sulfate Surfactants

The compositions hereof will preferably comprise alkyl sulfate, alkyl ethoxylated sulfate, or a mixture thereof. These materials have the respective formulae (I) $ROSO_3M$ and (II) $RO(C_2H_4O)_xSO_3M$, wherein R is alkyl or alkenyl of from about 8 to about 30 carbon atoms, x is 1 to 10, and M is H or a soluble salt-forming cation such as ammonium, alkanolamine, such triethanolamine, monovalent metals, such as sodium and potassium, and polyvalent metal cations, such as magnesium and calcium. The cation M, of the anionic surfactant should be chosen such that the anionic surfactant component is water soluble. Solubility of anionic surfactants, in general, will depend upon the particular anionic surfactants and cations chosen. As an aid to determining appropriate mixtures of anionic surfactants, the anionic surfactants should be chosen such that the Krafft temperature is about 15° C. or less, preferably about 10° C. or less, more preferably about 0° C. or less. It is also preferred that the anionic surfactant be soluble in the composition hereof.

Preferably, R has from about 10 to about 18 carbon atoms in both the alkyl and alkyl ethoxylated sulfates. The alkyl ethoxylated sulfates are typically made as condensation products of ethylene oxide and monohydric alcohols having from about 8 to about 24 carbon atoms. The alcohols can be derived from fats, e.g., coconut oil, palm kernel oil, or tallow, or can be synthetic. Such alcohols are preferably reacted with about 1 to about 10, more preferably from about 1 to about 4, most preferably from about 2 to about 3.5, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide.

The sulfate surfactant is preferably comprised of a combination of ethoxylated and nonethoxylated sulfates. The weight ratio of alkyl sulfate to alkyl ethoxylated sulfate is preferably from about 4:1 to about 1:10, more preferably from about 2:1 to about 1:8, even more preferably from about 1:1 to about 1:5, most preferably from about 1:2 to about 1:4. Weight ratios as described above are preferred for their ability to provide optimum combinations of lather, cleaning, and particulate anti-dandruff agent performance. Alkyl sulfates can provide excellent cleaning and lather performance. Alkyl ethoxylated sulfates can provide excellent cleaning performance, are mild to the skin, and can enhance deposition of the particulate anti-dandruff agent relative to alkyl sulfates.

Other Anionic Surfactants

A preferred type of anionic surfactant, especially for use in combination with anionic sulfate surfactants, are the N-acyl amino acid surfactants. N-acyl amino acid surfactants, for purposes hereof, include N-acyl hydrocarbyl acids and salts thereof, such as those represented by Formula III, as follows:

wherein: $R^1$ is a $C_8$–$C_{24}$ alkyl or alkenyl radical, preferably $C_{10}$–$C_{18}$; $R^2$ is —H, $C_1$–$C_4$ alkyl, phenyl, or —$CH_2COOM$, preferably $C_1$–$C_4$ alkyl, more preferably $C_1$–$C_2$ alkyl; $R^3$ is —$CR^4{}_2$— or $C_1$–$C_2$ alkoxy, wherein each $R^4$ independently is —H or $C_1$–$C_6$ alkyl or alkylester, and n is from 1 to 4, preferably 1 or 2; and M is —H or a cation as previously defined, preferably an alkali metal such as sodium or potassium.

A wide variety of N-acyl acid surfactants and their synthesis are described in *Anionic Surfactants, Part II, Surfactant Science Series, Vol. VII*, edited by Warner M. Linfield, Marcel Dekker, Inc. (New York and Basel), 1976; pp 581–617.

Especially preferred are compounds of Formula III wherein $R^2$ is methyl and $R^3$ is —$CH_2$—, and n is 1, which are known as the N-acyl sarcosinates, and acids thereof. Specific examples include lauroyl sarcosinate, myristoyl sarcosinate, cocoyl sarcosinate, and oleoyl sarcosinate, preferably in their sodium and potassium salt forms.

For the purposes of the surfactants described herein, it should be understood that the terms "alkyl" or "alkenyl" include mixtures of radicals which may contain one or more intermediate linkages such as ether or polyether linkages or non-functional substituents such as hydroxyl or halogen radicals wherein the radical remains of hydrophobic character.

Another type of anionic detersive surfactants are aliphatic sulfonates such as represented by the water-soluble salts of the organic, sulfuric acid reaction products of the general formula (IV):

wherein $R_1$ is chosen from the group consisting of a straight or branched chain, saturated aliphatic hydrocarbon radical having from about 8 to about 24, preferably about 12 to about 18, carbon atoms; and M is a cation, as previously described, subject to the same limitations regarding polyvalent metal cations as previously discussed. Important examples are the salts of an organic sulfuric acid reaction product of a hydrocarbon of the methane series, including iso-, neo-, and n-paraffins, having about 8 to about 24 carbon atoms, preferably about 12 about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12}$–$C_{18}$ paraffins (e.g. normal and secondary paraffins).

Additional examples of anionic detersive surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other synthetic anionic detersive surfactants of this variety are set forth in U.S. Pat. Nos. 2,486,921; 2,486,922; and 2,396,278.

Still other anionic detersive surfactants are in the class designated as succinates. This class includes such surface active agents as disodium N-octadecylsulfosuccinate; tetrasodium N-(1,2-dicarboxyethyl)- N-octadecylsulfosuccinate; diamyl ester of sodium sulfosuccinic acid; dihexyl ester of sodium sulfosuccinic acid; dioctyl esters of sodium sulfosuccinic acid.

Other suitable anionic detersive surfactants include olefin sulfonates having about 12 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example, by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having about 12 to about 24 carbon atoms, preferably about 14 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific alpha-olefin sulfonate mixture of the above type is described more fully in the U.S. Pat. No. 3,332,880, Pflaumer and Kessler, issued Jul. 25, 1967, incorporated herein by reference.

Another class of anionic detersive surfactants are the betaalkyloxy alkane sulfonates. These compounds have the following formula (V):

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Many additional synthetic anionic surfactants are described in *McCutcheon's Emulsifiers and Detergents, 1989 Annual*, published by M. C. Publishing Co., which is incorporated herein by reference. Also U.S. Pat. No. 3,929,678, Laughlin et al., issued Dec. 30, 1975, discloses many other anionic as well as other surfactant types and is incorporated herein by reference.

Preferred anionic detersive surfactants for use in the present shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric Surfactants

Amphoteric surfactants can optionally be used in the present compositions and processes. Examples of amphoteric surfactants which can be used in the present invention include those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate.

The amphoteric surfactant hereof include the imidazolinium amphoteric surfactants such as those depicted by Formula VI:

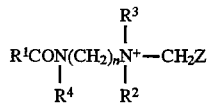  (VI)

wherein $R^1$ is $C_8-C_{22}$ alkyl or alkenyl, preferably $C_{12}-C_{16}$, $R^2$ is hydrogen or $CH_2CO_2M$, $R^3$ is $CH_2CH_2OH$ or $CH_2CH_2OCH_2CH\ COOM$, $R^4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation, such as alkali metal, alkaline earth metal, ammonium, or alkonol ammonium.

Suitable materials of this type are marketed under the tradename MIRANOL and are understood to comprise a complex mixture of species, and can exist in protonated and non-protonated species depending upon pH with respect to species that can have a hydrogen at $R^2$. The imidazolinum amphoteric surfactant hereof can be derived via an imidazolinium intermediate. However, it will be recognized by those skilled in the art that it needn't necessarily be derived via an imidazolinium.

Preferred amphoteric surfactants of Formula VII are monocarboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate.

Specific commercial products providing the inidazolinium derivative component of the present compositions include those sold under the trade names MIRANOL C2M CONC. N.P., MIRANOL C2M CONC. O.P., MIRANOL C2M SF, MIRANOL CM SPECIAL, MIRANOL ULTRA (Miranol, Inc.); ALKATERIC 2CIP (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHEROTERIC MS-2 (Scher Chemicals).

Amphoteric surfactants also include aminoalkanoates of the formula (VII):

  (VII) and iminodialkanoates of the formula (VIII):

  (VIII)

and mixtures thereof; wherein n and m are numbers from 1 to 4, R is $C_8-C_{22}$ alkyl or alkenyl, and M is hydrogen, alkali metal, alkaline earth metal, ammonium or alkanolammonium.

Examples of such amphoteric surfactants include n-alkylaminopropionates and n-alkyliminodipropionates. Such materials are sold under the tradename DERIPHAT by Henkel and MIRATAINE by Miranol, Inc. Specific examples include N-lauryl-beta-amino propionic acid or salts thereof, and N-lauryl-beta-imino-dipropionic acid or salts thereof.

Other amphoteric surfactants that can be used include betaine surfactants such as to be excluded include those represented by the Formula (IX):

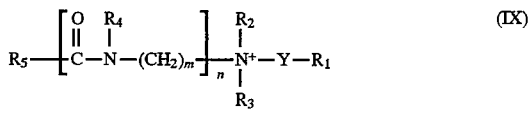  (IX)

wherein:

$R_1$ is a member selected from the group consisting of

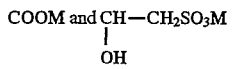

$R_2$ is $C_1-C_3$ alkyl or hydroxy $(C_1-C_3)$ alkyl;

$R_3$ is $C_1-C_3$ alkyl or hydroxy $(C_1-C_3)$ alkyl;

$R_4$ is a member selected from the group consisting of hydrogen and $C_1-C_3$ alkyl;

$R_5$ is $C_8-C_{20}$ alkyl or alkenyl;

Y is $C_1-C_3$ alkyl;

m is an integer from 2 to 7;

n is the integer 1 or 0;

M is hydrogen or a cation, such as an alkali metal or alkaline earth cation metal, ammonium, or alkanolamide.

The term "alkyl" or "hydroxyalkyl" means straight or branch chained, saturated, aliphatic hydrocarbon radicals and substituted hydrocarbon radicals such as, for example, methyl, ethyl, propyl, isopropyl, hydroxypropyl, hydroxyethyl, and the like.

Nonionic Surfactants

Nonionic detersive surfactants can also optionally be used in the present invention. Nonionic surfactants include those broadly defined as compounds produced by the condensation of alkylene oxide groups (hydrophilic in nature) with an organic hydrophobic compound, which may be aliphatic or alkyl aromatic in nature. Examples of preferred classes of nonionic detersive surfactants are:

1. The polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol.

2. Those derived from the condensation of ethylene oxide with the product resulting from the reaction of propylene oxide and ethylene diamine products.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals, the arrow in the formula is a conventional representation of a semipolar bond.

5. Long chain tertiary phosphine oxides corresponding to the following general formula:

$$RR'R''P \rightarrow O$$

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety.

7. Alkyl polysaccharide (APS) surfactants such as the alkyl polyglycosides. Such surfactants are described in U.S. Pat. No. 4,565,647, Lienado, issued Jan. 21, 1986, incorporated herein by reference, which discloses APS surfactants having a hydrophobic group with about 6 to about 30 carbon atoms and polysaccharide (e.g., polyglycoside) as the hydrophilic group. Optionally, there can be a polyalkylene-oxide group joining the hydrophobic and hydrophilic moieties. The alkyl group (i.e., the hydrophobic moiety) can be saturated or unsaturated, branched or unbranched, and unsubstituted or substituted (e.g., with hydroxy or cyclic rings).

8. Polyethylene glycol (PEG) glyceryl fatty esters, such as those of the formula $R(O)OCH_2CH(OH)CH_2(OCH_2CH_2)_nOH$ wherein n is from about 5 to about 200, preferably from about 20 to about 100, and R is an aliphatic hydrocarbyl having from about 8 to about 20 carbon atoms.

9. Polyhydroxy fatty acid amides of the formula:

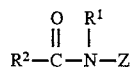

wherein: $R^1$ is H, $C_1$–$C_4$ hydrocarbyl, 2-hydroxy ethyl, 2-hydroxy propyl, or a mixture thereof, preferably $C_1$–$C_4$ alkyl, more preferably $C_1$ or $C_2$ alkyl, most preferably $C_1$ alkyl (i.e., methyl); and $R^2$ is a $C_5$–$C_{31}$ hydrocarbyl moiety, preferably straight chain $C_7$–$C_{19}$ alkyl or alkenyl, more preferably straight chain $C_9$–$C_{17}$ alkyl or alkenyl, most preferably straight chain $C_{11}$–$C_{15}$ alkyl or alkenyl, or mixture thereof; and Z is a polyhydroxyhydrocarbyl moiety having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z is a glycityl moiety. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —$CH(CH_2OH)$—$(CHOH)_{n-1}$—$CH_2OH$, —$CH_2$—$(CHOH)_2(CHOR')(CHOH)$—$CH_2OH$, where n is an integer from 3 to 5, inclusive, and R' is H or a cyclic or aliphatic monosaccharide, and alkoxylated derivatives thereof. Most preferred are glycityls wherein n is 4, particularly —$CH_2$—$(CHOH)_4$—$CH_2OH$.

In the above formula, $R^1$ can be, for example, N-methyl, N-ethyl, N-propyl, N-isopropyl, N-butyl, N-2-hydroxy ethyl, or N-2-hydroxy propyl.

$R^2$—CO—N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

Polyhydroxy fatty acid amides are disclosed, for example, in G.B. Patent Specification 809,060, published Feb. 18, 1959, by Thomas Hedley & Co., Ltd., U.S. Pat. No. 2,965,576, issued Dec. 20, 1960 to E. R. Wilson, and U.S. Pat. No. 2,703,798, Anthony M. Schwartz, issued Mar. 8, 1955, and U.S. Pat. No. 1,985,424, issued Dec. 25, 1934 to Piggott, each of which is incorporated herein by reference.

When used, the optional amphoteric and nonionic surfactants are typically present at levels of from about 0.05% to about 20%, more typically from about 0.1% to about 10%, preferably from about 0.5% to about 5%, although higher or lower levels can be used.

Particulate Anti-dandruff Agent

The shampoo compositions also contain one or more particulate anti-dandruff agents. A safe and effective amount of anti-dandruff active for control of dandruff of the scalp is used. Particulate antidandruff agents include, for example, sulfur, selenium sulfide, and pyridinethione salts. Preferred are heavy metal salts of 1-hydroxy-2-pyridinethione and selenium disulfide. The particulate anti-dandruff agents are in crystalline form and are insoluble in the compositions. In general, particulate antidandruff agents can be present at levels of about 0.1% to about 5%, preferably from about 0.3% to about 2%, by weight of the composition. The particular amount used is not critical as long as a safe and effective amount is used for controlling dandruff when the composition is used to shampoo the hair.

The particulate anti-dandruff agent has a volume average particle size of from about 0.35 microns to about 5 microns, preferably from about 0.40 microns to about 3 microns, more preferably from about 0.45 microns to about 2 microns. The volume average particle size is determined with a forward laser light scattering device which applies the Fraunhofer and Mie light scattering theories using a helium neon laser beam (632.8 nm) and 50 watt tungsten lamp, or equivalent. An example of suitable equipment includes the Horiba LA 910 light scattering particle size analyzer (Horiba Ltd., Kyoto, Japan). Preferably, at least about 50% of the particles will have a particle size within the above numerical range, more preferably at least about 75%.

Selenium sulfide is a staple item of commerce. Selenium sulfide is generally regarded as a compound having one mole of selenium and two moles of sulfur. However, it may take the form of a cyclic structure, $Se_xS_y$, wherein $x+y=8$.

U.S. Pat. No. 2,694,668, Baldwin et al., issued Nov. 16, 1954, U.S. Pat. No. 3,152,046, Kapral, issued Oct. 6, 1984; U.S. Pat. No. 4,089,945, Brinkman, issued May 16, 1978; and U.S. Pat. No. 4,885,107, Wetzel, issued Dec. 12, 1989, all incorporated herein by reference, disclose selenium disulfide as an active ingredient in antidandruff shampoo compositions.

If used, selenium sulfide is typically present in the shampoo compositions of this invention at a level of from about 0.1% to about 5.0%, preferably from about 0.3% to about 2.5%, more preferably from about 0.5% to about 1.5%, by weight of the composition.

Preferred pyridinethione anti-dandruff agents are water insoluble 1-hydroxy-2-pyridinethione salts. Preferred salts are formed from heavy metals such as zinc, tin, cadmium, magnesium, aluminum and zirconium. The most preferred metal herein is zinc. The most preferred active is the zinc salt of 1-hydroxy-2-pyridinethione, often referred to as zinc pyridinethione (ZPT). Other cations such as sodium may also be suitable. These types of anti-dandruff agents are well known in the art. 1-hydroxy-2-pyridinethione salts are disclosed for use in antidandruff shampoos in U.S. Pat. No. 2,809,971, Bernstein, issued Oct. 15, 1957, U.S. Pat. No. 3,236,733, Karsten et al., issued Feb. 22, 1966; U.S. Pat. No. 3,753,196 Parran, issued Aug. 21, 1973; U.S. Pat. No. 3,761,418, Parran, issued Sep. 25, 1973; U.S. Pat. No. 4,345,080, Bolich, issued Aug. 17, 1982; U.S. Pat. No. 4,323,683, Bolich et al., issued Apr. 6, 1982; U.S. Pat. No. 4,379,753, Bolich, issued April 12, 1983; and U.S. Pat. No. 4,470,982, Winkler, issued Sep. 11, 1984; all incorporated herein by reference.

The pyridinethione salts are preferably used at a level of from about 0.1% to about 3%, more preferably about 0.3% to about 2%, by weight of the shampoo composition.

Other particulate antidandruff actives include sulfur. Sulfur is typically used as an antidandruff agent at a level of from about 1% to about 5%, more preferably from about 2% to about 5%, by weight of the composition.

Small particle size anti-dandruff agents can be obtained from commercial suppliers or can be made by reducing larger particle size materials to the desired size by shear milling.

Cationic Polymer

The compositions hereof contain at least about 0.01%, by weight, of a stabilizing agent for the particulate antidandruff agent, preferably from about 0.01% to about 1%, more preferably from about 0.02% to about 0.5%, most preferably from about 0.02% to about 0.1%. Lower levels are contemplated as long as anti-dandruff agent suspension stability benefits are obtained. The stabilizing agent hereof is a shampoo soluble cationic polymer. It has been found that very low levels of such cationic polymer can effectively aid in suspension stability of the particulate anti-dandruff agent in the present shampoo compositions, with substantially reduced deposition trade-offs versus conventional suspension technologies. By "shampoo soluble" what is meant is that the cationic polymer is present in the shampoo in solubilized form. The shampoo soluble cationic polymers can exist in free ion form or as coacervates formed with the anionic surfactant.

The order in which the cationic polymers, anionic surfactant, and particulate anti-dandruff agent are incorporated into the final composition has been found to affect the final product. In particular, either the cationic polymer or the particulate anti-dandruff agent (but not both) should preferably be admixed in water with anionic surfactant before the cationic polymer and anti-dandruff agent are admixed together under aqueous conditions, during preparation of the composition. In other words, when the particulate anti-dandruff agent and cationic polymer exist together under aqueous conditions (i.e., in water) it should be in the presence of anionic surfactant. This is especially important for negatively charged anti-dandruff particles or anti-dandruff particles dispersed with a negatively charged dispersing aid, e.g., an anionic polymer or dispersing aid. It is also contemplated within the scope of the invention and the above description to prepare the composition under a variety of alternate conditions including admixing the cationic polymer and antidandruff agent under dry conditions, and then adding this mixture to an aqueous anionic surfactant solution. It is especially preferred to prepare an intermediate aqueous mixture containing the particulate anti-dandruff and anionic surfactant, and then add the cationic polymer.

In a preferred embodiment hereof, the compositions of the invention are made by the steps:

(a) preparing an aqueous mixture comprising:
 (i) anionic surfactant, (ii) water, and (iii) either the particulate anti-dandruff agent or the cationic polymer,
preferably the particulate anti-dandruff agent; and
(b) mixing into the aqueous mixture of (a) either the particulate anti-dandruff agent or the cationic polymer, whichever remains after step (a).

The components, preferred components, and the amounts and preferred amounts are as described above. The compositions made by this process are preferably substantially free of crystalline suspending agents, anionic polymeric suspending agents, amphoteric polymeric suspending agents, and nonionic polymeric suspending agents.

The concentration of anionic surfactant present in the aqueous surfactant solution should be sufficient to prevent agglommation of the cationic polymer and anti-dandruff agent. In general, the weight ratio of anionic surfactant:cationic polymer should preferably be at least about 20:1, preferably at least about 50:1, more preferably at least about 100:1, most preferably at least about 200:1.

The cationic polymers hereof will generally have a weight average molecular weight which is at least about 50,000, typically at least about 100,000, and is less than about 10 million. Preferably, the molecular weight is from about 200,000 to about 5 million, more preferably about 400,000 to about 1 million. The cationic polymers will have cationic nitrogen-containing moieties such as quaternary ammonium or cationic amino moieties, or a mixture thereof.

The cationic charge density is preferably at least about 0.3 meq/gram, more preferably at least about 0.6 meq/gram, even more preferably at least about 1.0 meq/gram, 1.2, most preferably at least about 1.2 meq/gram. The cationic charge density in general will be about 4 meq/gram or less, more generally about 3.0 meq/gram or less. Cationic charge density of the cationic polymer can be determined according to the Kjeldahl Method. Those skilled in the art will recognize that the charge density of amino-containing polymers in the final product may vary depending upon pH and the isoelectric point of the amino groups. The charge density should be within the above limits at the pH of intended use.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not intended to be exhaustive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the shampoo. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from ISP Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives.

Cationic polysaccharide polymer materials suitable for use herein include those of the formula:

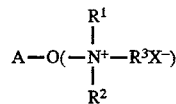

wherein:

A is an anhydroglucose residual group, such as a starch or cellulose anhydroglucose residual, R is an alkylene oxyalkylene, polyoxyalkylene, or hydroxyalkylene group, or combination thereof, $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

Cationic cellulose is available from Amerchol Corp. (Edison, N.J., USA) in their Polymer JR$^{TN}$, LR$^{TN}$, and LK$^T$-$_N$series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other cationic polymers that can be used include cationic guar gum derivatives, such as guar hydroxypropyltrimonium chloride (commercially available from Celanese Corp. in their Jaguar® series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein). Especially preferred cationic polymers include Polyquaternium 10.

Substantially Free of Conventional Suspendin Agents

The present compositions are preferably substantially free of crystalline suspending agents and anionic, amphoteric and nonionic polymeric thickening agents. In general, by "substantially free" what is meant is that the level of such suspending agents be about 0.5% or less, more preferably about 0.3% or less, even more preferably about 0.1% or less, most preferably 0% or no more than about 0.05%. Such 0 conventional suspending agents should preferably not be present or should only be present at sufficiently low levels such that they do not provide suspension stability to the antidandruff agent particles.

Crystalline suspending agents include long chain (e.g., $C_8$–$C_{22}$ preferably $C_{14}$–$C_{22}$, more preferably $C_{16}$–$C_{22}$) aliphatic groups, i.e., long chain acyl derivative materials and long chain amine oxides, as well as mixtures of such materials. Included are ethylene glycol long chain esters, alkanol amides of long chain fatty acids, long chain esters of long chain fatty acids, glyceryl long chain esters, long chain esters of long chain alkanolamides, and long chain alkyl dimethyl amine oxides, and mixtures thereof. Common suspending agents include, for example, ethylene glycol esters of fatty acids preferably having from about 14 to about 22 carbon atoms, more preferably 16–22 carbon atoms. Other suspending agents include $C_{16}$–$C_{22}$ alkanol amides of fatty acids and alkanol amides such as stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate); glyceryl esters (e.g., glyceryl distearate) and long chain esters of long chain alkanol amides (e.g., stearamide diethanolamide distearate, stearamide monoethanolamide stearate). Crystalline suspending agents also include long chain amine oxides such as alkyl ($C_{16}$–$C_{22}$) dimethyl amine oxides, e.g., stearyl dimethyl amine oxide. Other crystalline suspending agents include long chain acyl derivatives such as N,N-dihydrocarbyl ($C_{12}$–$C_{22}$) amido benzoic acid and soluble salts thereof (e.g., Na and K salts).

Polymeric suspending agents include any anionic, nonionic, or amphoteric polymeric materials that function as thickening agents in the present aqueous surfactant compositions. These include, for example, carboxyvinyl polymers, such as copolymers of acrylic acid crosslinked with polyallylsucrose as described in U.S. Pat. No. 2,798,053, Brown, issued Jul. 2, 1957, incorporated herein by reference. A carboxyvinyl polymer is an interpolymer of a monomeric mixture comprising a monomeric olefinically unsaturated carboxylic acid, and generally from about 0.01% to about 10% by weight of the total monomers of a polyether of a polyhydric alcohol, which polyhydric alcohol contains at least four carbon atoms to which are attached at least three hydroxyl groups, the polyether containing more than one alkenyl group per molecule.

Other polymeric suspending agents include those that can impart a gel-like viscosity to the composition, such as water soluble or colloidally water soluble polymers like cellulose ethers (e.g., carboxymethylcellulose hydroxyethyl cellulose), guar gum, xanthan gum, polyvinyl alcohol, polyvinyl pyrrolidone, hydroxypropyl guar gum, starch and starch derivatives. Other polymeric thickening agents to be excluded hereunder include acrylic acid and/or acrylate polymers, particularly the acrylic acid/$C_{10}$–$C_{30}$ acrylates crosslinked polymers such as the carbomer polymers. Polymeric suspending agents also include hydrophobically modified water soluble polymers, especially $C_{12}$–$C_{22}$ alkyl substutited cellulose polymers such as hydroxyethyl cellulose. Such polymers can be combined with surfactants or water soluble polymers to achieve a thickening, and consequently suspending, effect. Such polymers are disclosed for example in U.S. Pat. No. 5,106,609, issued Apr. 21, 1992 to Bolich et al., U.S. Pat. No. 5,100,658, issued Mar. 31, 1992 to Bolich et al., U.S. Pat. No. 5,104,646, issued Apr. 14, 1992 to Bolich et al., and U.S. Pat. No. 5,100,657, issued Mar. 31, 1992 to Ansher-Jackson et al., all of which are incorporated herein by reference.

Water

The compositions of the present invention will comprise from about 50% to about 91.89%, preferably from about 55% to about 89.68%, more preferably from about 60% to about 87.68%, by weight, of water.

The pH of the compositions hereof is not generally critical and may be in the range of from 2 to about 10, preferably from about 3 to about 9, more preferably from about 4 to about 8, most preferably from about 5.5 to about 7.5.

Conditioning Agents

Conditioning agents for the skin or hair may optionally be added to the compositions hereof. The conditioning agents for use herein include shampoo soluble conditioning agents and crystalline conditioning agents.

Soluble conditioning agents can include soluble silicone fluids, such as polyalkoxy silicones (e.g. polyethylene oxide and poly (ethylene/propylene) oxide modified polyalkylsiloxanes (preferably polymethyl siloxanes), such as dimethicone copolyol), $C_8$–$C_{18}$ fatty acids, $C_1$–$C_4$ esters of $C_8$–$C_{18}$ fatty acids, glycerine and other polyhydric alcohols, such as $C_3$–$C_6$ di-hydric alcohols and polyethylene glycol and poly ethylene/polypropylene glycol polymers.

Various of these conditioning agents may be soluble in the compositions up to a certain level, depending upon the particular ingredient chosen and the choice and levels of additional ingredients in the composition, particularly the type and amount of other surfactants, salts and the amount of water. The amount of such ingredients should preferably be chosen such that the entire amount added is soluble in the composition.

The polyether siloxane copolymers that may be used include, for example, a polyethylene oxide modified polydimethylsiloxane (e.g., Dow Corning DC-1248) although propylene oxide or mixtures of ethylene oxide and propylene oxide may also be used. The ethylene oxide and polypropylene oxide level must be sufficiently high to provide solubility in the composition hereof.

Cationic surfactants can also be used as optional ingredients. Cationic surfactants useful in compositions of the present invention, particularly the conditioner compositions, contain amino or quaternary ammonium hydrophilic moieties which are positively charged when dissolved in the aqueous composition of the present invention. Cationic surfactants among those useful herein are disclosed in the following documents, all incorporated by reference herein: M.C. Publishing Co., *McCutcheon's, Detergents & Emulsifiers*, (North American edition 1979); Schwartz, et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983.

Among the quaternary ammonium-containing cationic surfactant materials useful herein are those of the general formula:

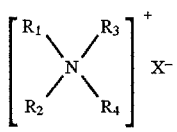

wherein $R_1$–$R_4$ are independently an aliphatic group of from about 1 to about 22 carbon atoms, aryl, or an alkoxy, polyoxyalkylene, alkylamido, hydroxyalkyl, or alkylaryl group having from about 1 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups. The longer chain aliphatic groups, e.g., those of about 12 carbons, or higher, can be saturated or unsaturated.

Quaternary ammonium salts include dialkyldimethylammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Other cationic surfactants include those wherein at least one of the $R_1$–$R_4$ radicals contains one or more hydrophilic moieties selected from alkoxy (preferably $C_1$–$C_3$ alkoxy), polyoxyalkylene (Preferably $C_1$–$C_3$ polyoxyalkylene), alkylamido, hydroxyalkyl, alkylester, and combinations thereof. Preferably, the cationic conditioning surfactant contains from 2 to about 10 nonionic hydrophile moieties located within the above stated ranges. For purposes herein, each hydrophilic amido, alkoxy, hydroxyalkyl, alkylester, alkylamido or other unit is considered to be a distinct nonionic hydrophile moiety. X is a soluble salt forming anion preferably selected from halogen (especially chlorine), acetate, phosphate, nitrate, sulfonate, and alkyl sulfate radicals.

Other quaternary ammonium salts useful herein are diquaternary ammonium salts, such as tallow propane diammonium dichloride.

Salts of primary, secondary and tertiary fatty amines are also suitable cationic surfactant materials. The alkyl groups of such amines preferably have from about 12 to about 22 carbon atoms, and may be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

Optional Ingredients

A variety of other optional ingredients are described below. The description below is exemplary in nature.

Such optional ingredients include, for example, preservatives such as benzyl alcohol, methyl paraben, propyl paraben and imidazolidinyl urea; cationic surfactants; block polymers of ethylene oxide and propylene oxide such as Pluronic F88 offered by BASF Wyandotte; salts such as sodium chloride, sodium sulfate; viscosity modifiers, such as ammonium xylene sulfonate; propylene glycol; polyvinyl alcohol; ethyl alcohol; pH adjusting agents such as citric acid, succinic acid, phosphoric acid, and salts thereof, sodium hydroxide, sodium carbonate, etc.; foam boosters such as $C_8$–$C_{18}$ mono- and di- ethanol amides, especially coco mono- and di- ethanol amides; perfumes; and dyes. These optional ingredients are typically used at levels of from about 0.01% to about 10% of the composition. This list of optional ingredients is not meant to be exclusive, and other optional components can be utilized.

METHOD OF USE

The present compositions are used in a conventional manner for cleaning hair and controlling dandruff on the scalp. The compositions hereof can also be affective for cleaning and controlling malodor associated with the skin (e.g. the body in general, including the underarm and crotch areas). An effective amount of the composition, typically from about 1 g to about 20 g of the composition, for cleaning hair, scalp, or other region of the body, is applied to the hair, scalp, or other region that has preferably been wetted, generally with water, and then rinsed off. Application to the hair typically includes working the composition through the hair and scalp such that most or all of the hair and scalp is contacted with the composition.

EXAMPLES

The following Examples further describe and demonstrate the preferred embodiments within the scope of the present invention. The Examples are given solely for the purpose of illustration and are not to be construed as limitations of the present invention as many variations thereof are possible without departing from its spirit and scope.

Examples I-XX

The following examples exemplify shampoo compositions of the present invention.

The compositions are prepared as follows.

If fatty alcohol, and/or CMEA are used, about one-third to all of the total alkyl sulfate surfactant (ammonium laureth-3 sulfate (added as a 26 wt. % solution) and/or ammonium lauryl sulfate (added as a 25 wt. % solution)) is added to a jacketed mix tank and heated to about 65° C. The fatty alcohol and/or CMEA are added with slow agitation to form a surfactant solution. Add the preservative to the tank and allow to disperse. Cool to about 35° C. The remainder of the ammonium laureth sulfate, lauryl sulfate and other ingredients, are then added with agitation to ensure a homogeneous mixture. Polyquaternium 10 is dispersed in water as a 1% aqueous solution before addition to the final mix. Once all ingredients have been added, ammonium xylene sulfonate or additional sodium sulfate may be added to the mixture to thin or thicken respectively to achieve a desired product viscosity. Preferred viscosities range from about 2500 to about 6000 cS at 25° C. (as measured by a Wells-Brookfield cone and plate viscometer at a shear rate of 15/s).

The compositions of the examples can provide excellent in-use hair cleaning, lather, delivery of anti-dandruff active and dandruff control.

| Component (%, by weight, of composition) | Example Number | | | | |
|---|---|---|---|---|---|
| | I | II | III | IV | V |
| Ammonium Laureth 3 Sulfate | 13.5 | 13.5 | 16 | 8 | 16 |
| Ammonium Lauryl Sulfate | 4.5 | 4.5 | 1.5 | 8 | 3 |
| Sodium Lauryl Sarcosinate | 1.5 | 2 | 3.75 | 2.5 | 0 |
| Cocoamidopropyl Betaine | 1.5 | 1 | 0 | 0 | 2 |
| Sodium Sulfate | 0.8 | 0.8 | 0.8 | 0.8 | 0.8 |
| Polyquaternium 10[1] | 0.025 | 0.025 | 0.02 | 0.05 | 0.05 |
| Perfume Solution | 0.65 | 0.65 | 0.4 | 0.5 | 0.25 |
| DMDM Hydantoin | 0.2 | 0.2 | 0.3 | 0.3 | 0.3 |
| Zinc Pyridinethione[3] | 1 | 0.5 | 1 | 0.5 | 0.5 |
| Dye (ppm) | 10 | 10 | 10 | 20 | 20 |
| Water | QS | QS | QS | QS | QS |

| Component (%, by weight, of composition) | Example Number | | | | |
|---|---|---|---|---|---|
| | VI | VII | VIII | IX | X |
| Ammonium Laureth 3 Sulfate | 11.5 | 14.5 | 16 | 6 | 16 |
| Ammonium Lauryl Sulfate | 4.5 | 2.5 | 3.5 | 8 | 2 |
| Sodium Lauryl Sarcosinate | 1.5 | 2 | 3.75 | 2.5 | 2 |
| cocoamidopropyl Betaine | 1.5 | 1.5 | 0 | 0 | 1.5 |
| Sodium Sulfate | 0.8 | 0.8 | 0.8 | 0.8 | 0.8 |
| Coconut (C12–C14) Fatty Alcohol | 0.2 | 0 | 0.35 | 0 | 0 |
| Polyquaternium 10[1] | 0.025 | 0.02 | 0.025 | 0.05 | 0.05 |
| Perfume Solution | 0.65 | 0.65 | 0.4 | 0.5 | 0.25 |
| DMDM Hydantoin | 0.2 | 0.2 | 0.3 | 0.3 | 0.3 |
| Zinc Pyridinethione[3] | 1 | 0.5 | 1 | 0.5 | 1.5 |
| Dye (ppm) | 10 | 10 | 10 | 20 | 20 |
| Water | QS | QS | QS | QS | QS |

| Component (%, by weight, of composition) | Example Number | | | | |
|---|---|---|---|---|---|
| | XI | XII | XIII | XIV | XV |
| Ammonium Laureth (3) Sulfate | 18 | 0 | 15 | 15 | 10 |
| Ammonium Lauryl Sulfate | 0 | 12 | 3 | 5 | 5 |
| Sodium Lauryl Sarcosinate | 3 | 0 | 2.3 | 1 | 5 |
| Cocoamidopropyl Betaine | 1 | 3 | 0 | 1.5 | 0 |
| Sodium Sulfate | 0.8 | 0.8 | 0.8 | 0.8 | 0.8 |
| Coconut (C12–C14) Fatty Alcohol | 0.2 | 0.2 | 0 | 0.35 | 0 |
| Polyquaternium 10[1] | 0.1 | 0.2 | 0.25 | 0.2 | 0.2 |
| Perfume Solution | 0.9 | 0.35 | 0.3 | 0.7 | 1.1 |
| DMDM Hydantoin | 0.2 | 0.2 | 0.4 | 0.4 | 0.4 |
| Zinc Pyridinethione[3] | 0.5 | 1 | 0.75 | 1 | 1 |
| Dye (ppm) | 10 | 10 | 10 | 20 | 20 |
| Water | QS | QS | QS | QS | QS |

| Component (%, by weight, of composition) | Example Number | | | | |
|---|---|---|---|---|---|
| | XVI | XVII | XVIII | XIX | XX |
| Ammonium Laureth (3) Sulfate | 18 | 0 | 15 | 13 | 10 |
| Ammonium Lauryl Sulfate | 0 | 12 | 3 | 5 | 5 |
| Sodium Lauryl Sarcosinate | 3 | 0 | 2.3 | 1 | 5 |
| CMEA | 0.75 | 3 | 1.5 | 2 | 1 |
| Cocoamidopropyl Betaine | 1 | 0 | 0 | 1.5 | 0 |
| Sodium Sulfate | 0.8 | 0.8 | 0.8 | 0.8 | 0.8 |
| Coconut (C12–C14) Fatty Alcohol | 0.2 | 0.2 | 0 | 0.35 | 0 |
| Polyquaternium 10[1] | 0.1 | 0.2 | 0.25 | 0.2 | 0.2 |
| Perfume Solution | 0.9 | 0.35 | 0.3 | 0.7 | 1.1 |
| DMDM Hydantoin | 0.2 | 0.2 | 0.4 | 0.4 | 0.4 |
| Zinc Pyridinethione[2] | 0.5 | 1 | 0.75 | 1 | 1 |
| Dye (ppm) | 10 | 10 | 10 | 20 | 20 |
| Water | QS | QS | QS | QS | QS |

[1]UCARE Polymer JR-30M, commercially available from Union Carbide Corporation.
[2]Volume average particle size, 2.5 microns, available from Olin Chemicals (Rochester, N.Y., USA).
[3]Zinc Omadine™ available from Olin Chemicals BV (Dublin, Ireland), volume aveage particle size 0.45–0.5 microns.

What is claimed is:

1. An anti-dandruff shampoo composition comprising:
   (a) from about 8% to about 40%, by weight, of anionic detersive surfactant;
   (b) from about 0.1% to about 5%, by weight, of particulate anti-dandruff agent having a volume average particle size of from about 0.35 microns to about 5 microns;
   (c) from about 0.01% to about 1%, by weight, of a stabilizing agent for said anti-dandruff agent, said stabilizing agent being a shampoo soluble cationic polymer; and
   (d) from about 50% to about 91.89%, by weight, water; wherein said shampoo composition contains not greater than about 0.1%, by weight, of suspending agents selected from the group consisting of crystalline suspending agents, and anionic, amphoteric, and nonionic polymeric suspending agents.

2. An anti-dandruff shampoo composition as in claim 1, wherein said cationic polymer has a weight average molecular weight of at least about 50,000.

3. An anti-dandruff shampoo composition as in claim 2, wherein said cationic polymer has a weight average molecular weight of at least about 100,000 and a charge density of at least about 0.3 meq/g.

4. An anti-dandruff shampoo composition as in claim 3, wherein said cationic polymer has a weight average molecular weight of from about 200,000 to about 5,000,000 and a charge density of from about 0.6 meq/g to about 4 meq/g.

5. An anti-dandruff shampoo composition as in claim 1, wherein said anti-dandruff agent has a volume average particle size of from about 0.4 microns to about 3 microns.

6. An anti-dandruff shampoo composition as in claim 4, wherein said anti-dandruff agent has a volume average particle size of from about 0.4 microns to about 3 microns.

7. An anti-dandruff shampoo composition as in claim 1, wherein said anti-dandruff agent is selected from the group consisting of sulfur, selenium sulfide, pyridinethione salts, and mixtures thereof.

8. An anti-dandruff shampoo composition as in claim 7, wherein said anti-dandruff agent is zinc pyridinethione.

9. An anti-dandruff shampoo composition as in claim 5, wherein said anti-dandruff agent is zinc pyridinethione.

10. An anti-dandruff composition as in claim 1, wherein said composition contains about 0.05%, by weight, or less of said suspending agents.

11. An anti-dandruff shampoo composition as in claim 1, wherein said composition comprises:

(a) from about 10% to about 30% of said anionic detersive surfactant;

(b) from about 0.3% to about 2% of said anti-dandruff agent; and (c) from about 0.02% to about 0.5% of said stabilizing agent;

wherein said cationic polymer has a charge density of at least about 0.3 meq/g.

12. A method for making an anti-dandruff shampoo composition comprising mixing;

(a) from about 8% to about 40%, by weight, anionic detersive surfactant;

(b) from about 0.1% to about 5%, by weight, of particulate anti-dandruff agent having a volume average particle size of from about 0.35 microns to about 5 microns;

(c) from about 0.01% to about 1%, by weight, of stabilizing agent for said anti-dandruff agent, said stabilizing agent being a shampoo soluble cationic polymer; and (d) from about 50% to about 91.89%, by weight, water; wherein said particulate anti-dandruff agent and said cationic polymer are admixed in water in the presence of anionic detersive surfactant, and said composition contains not greater than about 0.1% by weight, of crystalline suspending agents and anionic, amphoteric, and nonionic polymeric suspending agents.

13. An anti-dandruff shampoo composition made according to the method of claim 12.

14. An anti-dandruff shampoo composition as in claim 1, wherein said stabilizing agent comprises a shampoo soluble cationic polymer having nitrogen-containing moieties.

15. An anti-dandruff shampoo composition as in claim 14, wherein the nitrogen-containing moieties are quaternary ammonium moieties or cationic amino moieties.

16. An anti-dandruff shampoo composition as in claim 14, wherein the shampoo soluble cationic polymer comprises a cationic cellulose polymer, a cationic starch polymer or a cationic guar gum.

17. An anti-dandruff shampoo composition as in claim 14, wherein the shampoo soluble cationic polymer comprises units formed from one or more monomers selected from the group consisting of dialkylaminoalkyl acrylate, dialkylaminoalkyl methacrylate, monoalkylaminoalkyl acrylate, monoalkylaminoalkyl methacrylate, dialkylaminoalkyl acrylamide, dialkylaminoalkyl methacrylamide, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings selected from the group consisting of pyridinium, imidazolium, and quaternized pyrrolidone, wherein alkyl portions of said monomers are $C_1$–$C_7$ alkyls.

* * * * *

UNITED STATES PATENT AND TRADEMARK OFFICE
CERTIFICATE OF CORRECTION

PATENT NO. : 5,624,666

DATED : April 29, 1997

INVENTOR(S) : Timothy W. Coffindaffer et al.

It is certified that error appears in the above-indentified patent and that said Letters Patent is hereby corrected as shown below:

At column 6, line 47 "Pfiaumer" should read --Pflaumer--.

At column 6, line 50 "betaalkyloxy" should read --beta alkyloxy--.

At column 9, line 50 "moleties" should read --moieties--.

At column 9, line 54 "Lienado" should read --Llenado--.

At column 9, line 60 "moleties" should read --moieties--.

At column 10, line 32 "$(CHOH)_{n-11}$" should read --$(CHOH)_{n-1}$--.

At column 11, line 26 "1954, U.S." should read --1954; U.S.--.

At column 11, line 48 "1957, U.S." should read --1957; U.S.--.

At column 12, line 4 "antidandruff" should read --anti-dandruff--.

UNITED STATES PATENT AND TRADEMARK OFFICE
CERTIFICATE OF CORRECTION

PATENT NO. : 5,624,666

DATED : April 29, 1997

INVENTOR(S) : Timothy W. Coffindaffer et al.

It is certified that error appears in the above-indentified patent and that said Letters Patent is hereby corrected as shown below:

At column 13, line 21 "CI" should read --Cl--.

At column 13, line 22 "CI" should read --Cl--.

At column 14, lines 62-63 "$LK^T$-Nseries" should read --$LK^{TN}$ series--.

At column 15, line 15 "Suspendin" should read --Suspending--.

At column 15, line 24 "Such 0" should read --Such--.

At column 17, line 42 "moleties" should read --moieties--.

At column 17, line 46 "moleties" should read --moieties--.

At column 21, line 10 "mixing;" should read --mixing:--.

Signed and Sealed this

Sixteenth Day of September, 1997

Attest:

Attesting Officer

BRUCE LEHMAN

Commissioner of Patents and Trademarks